United States Patent [19]

Saika

[11] Patent Number: 5,734,065

[45] Date of Patent: Mar. 31, 1998

[54] THIOPHENE DERIVATIVE AND THE POLYMER THEREOF AND METHODS FOR PRODUCTION THEREOF

[75] Inventor: Tetsuyuki Saika, Suita, Japan

[73] Assignee: Research Development Corporation of Japan, Japan

[21] Appl. No.: 519,814

[22] Filed: Aug. 25, 1995

[30] Foreign Application Priority Data

Aug. 25, 1994 [JP] Japan .................................. 6-201134

[51] Int. Cl.$^6$ .......................... C07D 409/06; C08F 2/46; C08G 77/22; C08G 75/00

[52] U.S. Cl. ................ 549/59; 522/168; 528/30; 528/380

[58] Field of Search .................. 549/59; 522/168; 528/30, 380

[56] References Cited

PUBLICATIONS

Saika et al., J. Chem. Soc., Chem. Commun., 1994, No. 18, 2123–2124.
Tour et al., Macromolecules, 1992, vol. 25, 1901–1907.

*Primary Examiner*—Deborah Lambkin
*Attorney, Agent, or Firm*—Wenderoth, Lind & Ponack

[57] ABSTRACT

The present invention provides a thiophene derivative and the polymer thereof as expressed in the following formulas, which will respond to light and electricity and which are best suited for use as photorecording materials and light-electricity conversion elements.

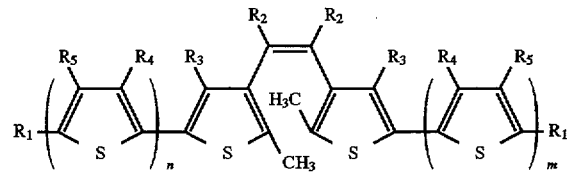

where n and m are independent integral numbers greater than 0; $R_1$ is a hydrogen atom, a halogen atom or a trialkylsilyl group; the $R_2$s together with the ethylenic linkage form a ring and said $R_2$s taken together are an optionally substituted alkylene group or —COOCO— or the $R_2$s independently represent cyano; and $R_3$, $R_4$ and $R_5$ are hydrogen or alkyl.

13 Claims, 2 Drawing Sheets

THIOPHENE DERIVATIVE AND THE POLYMER THEREOF AND METHODS FOR PRODUCTION THEREOF

FIELD OF THE INVENTION

The present invention relates to a novel thiophene derivative and the polymer thereof and methods for producing the same. More specifically, it relates to a thiophene derivative and the polymer thereof that will respond to optical and electric stimuli and are accordingly useful as photorecording materials and light-electricity response devices.

PRIOR ARTS AND THE PROBLEMS

Chemical compounds which will vary their colors in response to light irradiation are known as photochromic compounds. Various photochromic compounds have been proposed for use in photo-recording, or as photo-memories, photo-switches, actinometers or display materials. They include azobenzenes, spiropyranes, spirooxazines, and luigides. However, these conventional photochromic materials had disadvantages; they are thermally unstable during a color development phase and are subject to gradual disappearance of color even at room temperatures, thus leading to a consequent decrease in recording stability. And, they possessed less than sufficient repetitious durability, and hence became degraded in due course while being subjected to repeated phases of color development and disappearance.

One example of the conventionally known photochromic compounds which possess thermal stability during a color development phase and relatively good repetitious durability is diarylethenes; they are found in the description of the Japanese Provisional Patent Publication No. 135977/91, No. 261762/91, No. 261947/91, No. 51379/91, No. 59025/91, and No. 247034/91. They still suffer from the problems with absorption wavelength and sensitivity, though. In particular, in order to apply semiconductor laser technology to photorecording, there has been need for photochromic compounds having an absorption at wavelengths greater than 800 nm, but they are not yet to be realized.

Chemical compounds that will change color in response to electrical stimuli, on the other hand, are referred to as electrochromic compounds, and are considered promising as display materials. During recent years, $\pi$ conjugate high polymers have been found to show electochemically doped or undoped phenomena with electrochromism and to be electrically conductive while in a doped state. Examples of $\pi$ conjugate high polymers that exhibit such properties polythiophene, polypyrole and polyaniline. Oligomers of thiophene and pyrole are also known to show electrochromism, and additionally can be easily polymerized into high polymers.

Nevertheless, these conventional electrochromic materials were nothing short of satisfactory in stability and durability, and had much to improve in electrical response.

As compounds which show both photochromism and electrochromism, anthraquinones having an azo group are disclosed in the Japanese Provisional Patent Publication No. 88553/87. Photochromism at the azobenzene site was such that they were so thermally unstable during a color development phase that they showed gradual disappearance of color even at room temperatures, thereby leading to a consequent degradation in their recording stability.

SUMMARY OF THE INVENTION

To overcome these problems, the present invention has the objective of providing new compounds, as well as methods for producing the same, which can respond both to electric and optical stimuli, and which, hence, are thermally stable while they are developing color and possess relatively good repetitious durability.

To provide solutions to the problems referred to above, by polymerizing the aryl site of diarylethene into a $\pi$ conjugate oligomer, present invention provides a novel thiophene derivative and the polymer thereof which combine two properties: photochromism, a phenomenon in which they are thermally stable during a color development phase and show relatively outstanding repetitious durability, and electric response which they show at the $\pi$ conjugate oligomer site.

The present invention provides a thiophene derivative expressed by the Formula (I).

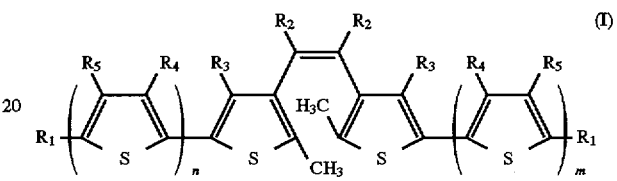

(Where n and m are independent integral numbers greater than 0; $R_1$ is a hydrogen atom, a halogen atom or a trialkylsilyl group; $R_2$ are an alkylene group which may possess a substituent group or a —COOCO-group forming ring with an ethylenic linkage, respectively, or exclusively a cyno group; and $R_3$, $R_4$ and $R_5$ are a hydrogen atom or an alkyl group, respectively.)

DETAILED DESCRIPTION OF THE INVENTION

Figure 1:
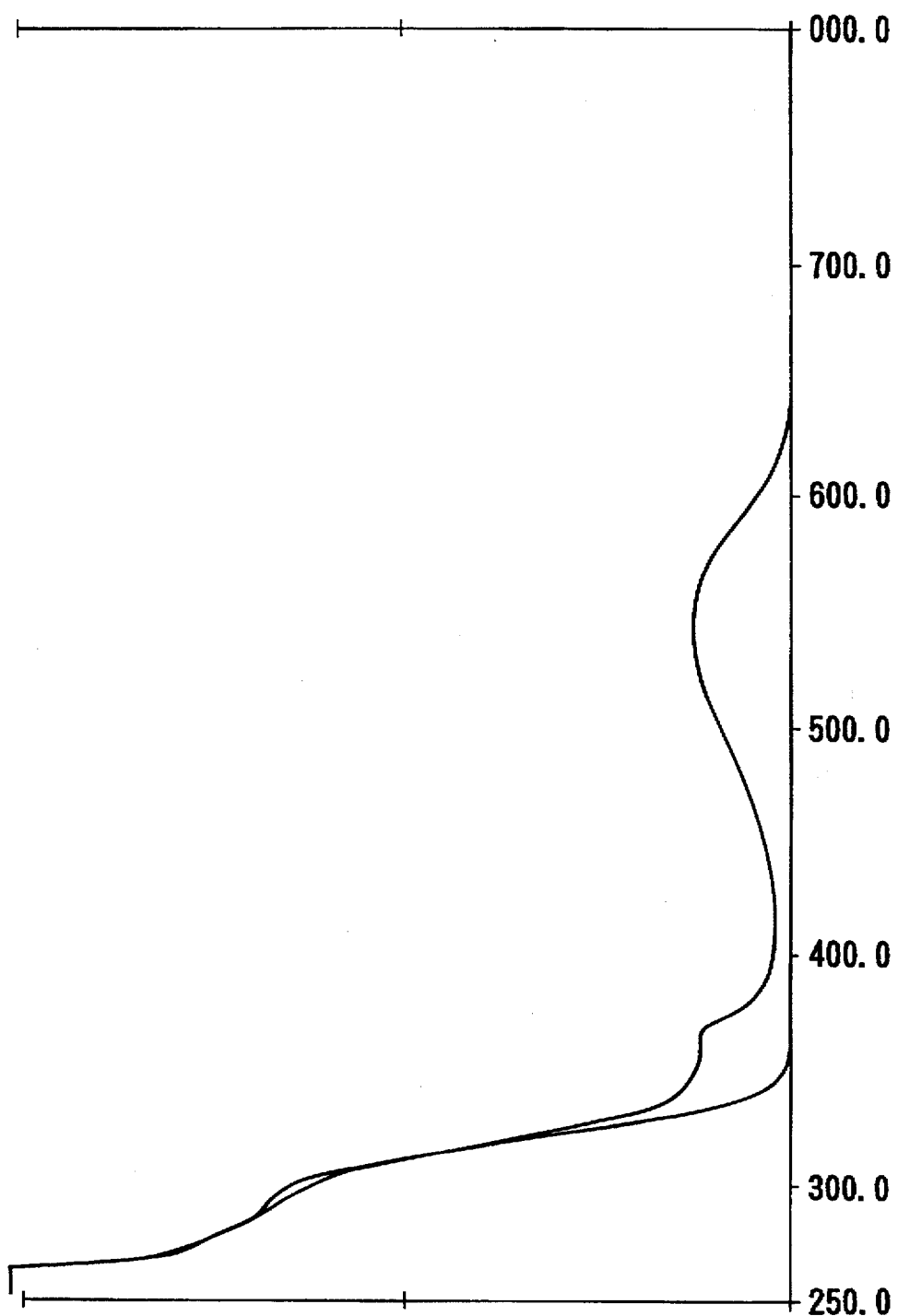
FIG. 1 shows a state in absorption spectrum as an example.

This invention is a method for producing the thiophene derivative, as described in Formula (I), wherein $R_1$ is hydrogen atom or a trialkylsilyl group larger than 0; $R_1$ is a hydrogen atom, a halogen atom or a trialkylsilyl group; the $R_2$s to form a ring with an ethylenic linkage and represent an optionally substituted alkylene or a —COOCO— group, or the $R_2$s independently are cyano; and $R_3$, $R_4$ and $R_5$ are a hydrogen atom or an alkyl group, respectively.)

This invention provides a method for producing the thiophone derivative, represented by Formula (I), wherein $R_1$ is a hydrogen atom or a trialkylsilyl group comprising the step of:

allowing an alkene compound expressed by the following Formula (II) to react with a thiophone compound expressed by Chemical Formula (III) below.

(where $R_2$s are an alkylene group which may possess a substituent group or a —COOCO— group forming a ring with an ethylenic linkage, respectively, or, exclusively, a cyano group in every case, and Z is a halogen atom.)

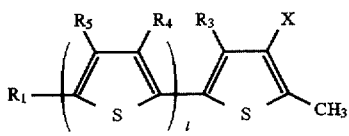

(where, 1 shows any integral number greater than 0;R is a hydrogen atom, a halogen atom or a trialkylsilyl group; $R_3$, $R_4$ and $R_5$ are independent constituents, and are a hydrogen atom or an alkyl group, respectively; and X is a halogen atom.)

This invention provides, in particular, a method for producing a thiophene derivative, wherein an alkene compound by Formula (II) is perfluorocycloalkene which can be expressed by Formula (IV):

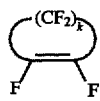

(where, k is an integral number ranging from 2 to 4.) The instant invention also provides a method for producing a thiophene derivative, wherein $R_1$ is a hydrogen atom or a trialkylsilyl group, comprising the step of:

allowing an alkene compound expressed by the following Formula (V) to react with a thiophene compound expressed by Formula (VI) below.

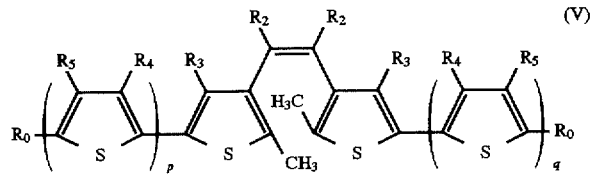

(where p and q are independent integral numbers greater than 0; $R_0$ is a halogen atom; $R_2$s are an alkylene group which may possess a substituent group or a —COOCO— group forming a ring with an ethylenic linkage, respectively, or, exclusively, a cyano group; and $R_3$, $R_4$ and $R_5$ are independent constituents, and are a hydrogen atom or an alkyl group, respectively.)

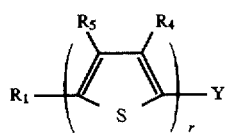

(where, r shows any integral number greater than 0;$R_4$ and $R_5$ are independent constituents, and are a hydrogen atom or an alkyl group, respectively; Y shows a —B(OH)$_2$, trialkyl tin residue or a halogenated magnesium residue; and $R_1$ is a hydrogen atom or a trialkylsilyl group.)

The present invention also provides three methods for producing a thiophene derivative. The first method (for producing a thiophene derivative), wherein $R_1$ is a halogen atom, comprises the step of substituting a hydrogen atom or a trialkylsilyl group, a constituent element expressed as $R_1$ in Formula (I), by a halogen atom.

The second (method for producing a thiophene derivative), wherein $R_1$ is a hydrogen atom, comprises the step of causing an acid decomposition reaction of a trialkylsilyl group to give a hydrogen atom as $R_1$ in Formula (I), and The third (method for producing a thiophene derivative), wherein $R_1$ is a trialkylsilyl group, comprises the step of substituting a halogen atom as expressed as $R_1$ in Formula (I) by a trialkylsilyl group.

Additionally, the instant inventions also provides a thiophene derivative, a photoisomer of a thiophene derivative represented by Formula (I) and which can be expressed by Chemical Formula (VII):

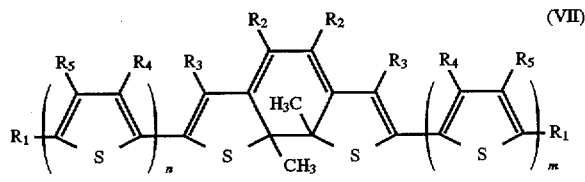

The present invention further provides a thiophene derivative polymer which has a building block expressed by the following Formulae (VIII) and (IX), and a method for producing the same, comprising the steps of polymerizing electrolytically or through oxidation of a thiophene derivative expressed by the following Formula (X) or (XI),

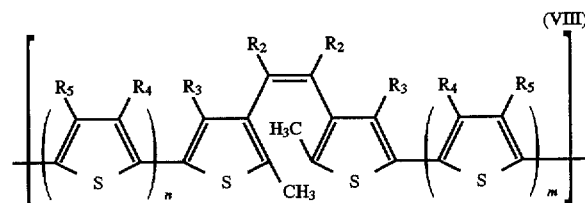

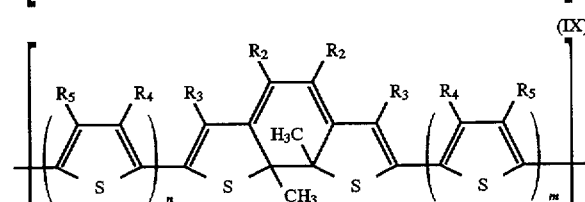

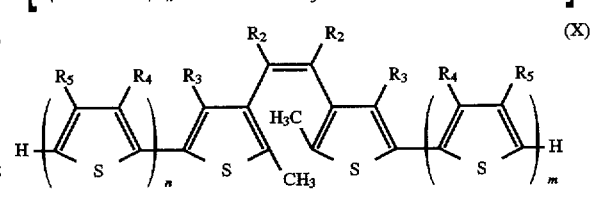

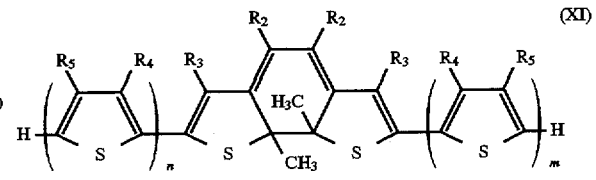

as well as a method for producing said polymer, comprising the step of chemically polymerizing a thiophene derivative expressed by the following formula (XII) or (XIII):

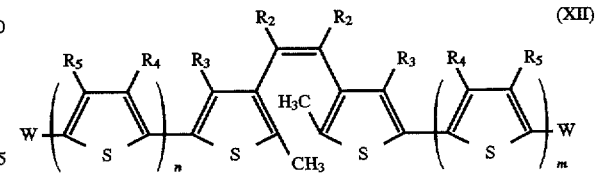

-continued

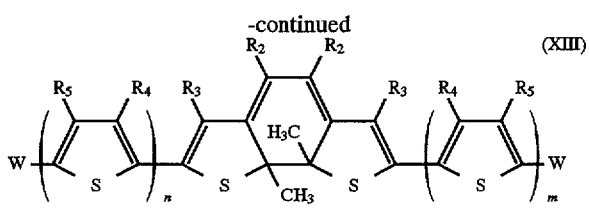

(Where, W is a halogen atom.)

The thiophene derivative expressed by Formula (1) above of this invention is characterized primarily by two thiophene oligomer chain where the coefficients n, m are independent integral numbers larger than 0, preferably 0–6, and by a carbon-carbon double bond of alkene joining them.

$R_1$ is hydrogen atom or halogen atom which may be chlorine, bromine, or iodine, or trialkylsilyl group which typically includes trimethylsilyl, triethylsilyl, tripropylsilyl, tributylsilyl, and t-butyldimethylsilyl.

$R_2$ for alkylene group, which may possess a substituent to form a ring with an ethylene linkage preferably forms a carbon ring with $C_4$ or greater. The substituent may be a halogen atom including fluorine, an ether group, an ester group, an alkylamino group, a nitro group, or a cyano group. Alternatively, $R_2$ may be a —COOCO— group which make acid anhydride ring, or it may be a cyano group, exclusively.

$R_3$, $R_4$ and $R_5$ for alkyl groups may preferably be in the order of $C_1$ to $C_{20}$. Examples include methyl, groups, propyl groups, butyl groups, pentyl groups, hexyl groups, heptyl groups, octyl groups, nonyl groups, decyl groups, octadecyl groups, or dodecyl groups.

An alkene compound represented by Formula (II) is reacted with a thiophene compound in Formula (III) to produce the thiophene derivative represented by Formula (I), the target compound of the instant invention. In the production process, it is possible to make a lithio product of the thiophene oligomer in Formula (III) using an alkyl lithium, and then to add to the reaction solution of the alkene compound expressed by Formula (II), for example, perfluorocycloalkene, to induce a coupling reaction. The alkyl lithiums that can be most advantageously used for the reaction are n- butyl lithium, s-butyl lithium, or t-butyl lithium. It is preferable to use the alkyl lithium in 1 to 1.2 equivalent amount to thiophene oligomer. Diethylether, tetrahydrofuran or other ether solvents are best suited reaction solvents. It is desirable that the production of the lithio product with the alkyl lithium is made at low temperatures, most preferably, −80° C. to −40° C. It is also desirable to complete the reaction within one hour, preferably in 5 to 30 minutes. If the coupling reaction is carried out by adding perfluorocycloalkene, the reaction temperature should be −80° C. to −40° C. at the start of the reaction, and increased slowly until room temperature to complete the reaction. It is most preferred to complete the reaction in one to 20 hours. Octafluorocyclopentene, hexafluorocyclobutene, and decafluorocyclohexane are among the most preferred candidates of perfluorocycloalkene. The perfluorocycloalkene is used in equivalents of 0.3 to 1 to the thiophene oligomer, the starting substance. The thiophene oligomer replaces two vinyl-coordination fluorine atoms in perfluorocycloalkene to give a thiophene derivative having a dialylethene structure represented by Formula (I). The product is washed off to remove reaction solvent, and then is purified by the normal treatment process to produce the thiophene derivative expressed by Formula (I), In the case of an excess of perfluorocycloalkenes, a by-product in which the perfluorocycloalkene is replaced by one thiophene oligomer can be obtained. The thiophene derivative was produced by a reaction of the by-product with a lithio product of the thiophene olibomer, too.

In the production of above thiophene derivatives, the target compound of the present invention, it is possible to extend the thiophene oligomer side chains from the compound as expressed by Formula (I) where $R_1$ for halogen atom is chlorine, bromine or iodine. This means that a compound expressed by Formula (I) where $R_1$ for halogen atom is chlorine, bromine or iodine is caused to react with a thiophene compound expressed by Formula (IV), giving the derivatives with more side chains. Specific examples of the compounds used for this reaction and expressed by Formula (I) where $R_1$ is chlorine, bromine and iodine are: 1,2-bis(5-bromo-2-methyl-3-thienyl) hexafluorocyclopentene, 1,2-bis (5-chloro-2-methyl-3-thienyl) hexafluorocyclopentene, 1,2-bis (5-iodo-2-methyl-3-thienyl) hexafluorocyclopentene, 1,2-bis(5-bromo-2,4-dimethyl-3-thienyl) hexafluorocyclopentene, 1,2-bis (5-chloro-2,4-dimethyl-3-thienyl) hexafluorocyclopentene, 1,2-bis (2,4-dimethyl-5-iodo-3-thienyl) hexafluorocyclopentene, 1,2-bis (5-bromo-4-butyl-2-methyl-3-thienyl) hexafluorocyclopentene, 1,2-bis (4-butyl-5-chloro-2-methyl-3-thienyl) hexafluorocyclopentene, 1,2-bis (5-iodo-4-butyl-2-methyl-3-thienyl) hexafluorocyclopentene, 1,2-bis (5-bromo-2-methyl-4-stearyl-8-thienyl) hexafluorocyclopentene, 1,2-bis (5-bromo-2-methyl-3-thienyl) octafluorocyclopentene, 1,2-bis (5-iodo-2-methyl-4-stearyl-3-thienyl) octafluorocyclopentene, and 1,2-bis(5-iodo-2-methyl-3-thienyl) octafluorocyclopentene. In the compound expressed by the general formula (VI), Y is an organic metal substituent group, known to couple with allyl halide, and may be a boric acid residue, boric acid ester residues, such as dibutoxy, and dimethoxy boric acid, trialkyl tin esidues such as tributyl and trimethyl tin, or magnesium halide residues, such as magnesium bromide and magnesium chloride.

The compound expressed by Formula (VI) is used in 2 to 3 equivalents per unit of the halogen compound according to Formula (V). The best solvents for the reaction are diethylether, tetrahydrofuran, dioxane, dimethoxy ethane and other ether solvents, and toluene, xylene and other aromatic solvents. Use of the following catalysts for the reaction often brings about favorable results: palladium tetrakis (triphenylphosphine), palladium tris(dibenzylidene acetone), carobnyltris(triphenylphosphine) palladium, bis (t-butylisocyanate) palladium and other palladium catalysts, or bis nickel(aceacetyl acetone), nickel tetrakis (triphenylphosphine), nickel dichlorobis (triphenylphosphine) and other nickel catalysts. It is desirable, for instance, to add 0.1 to 10 percent of the halogen compound expressed by Formula (V), as a substrate material. The reaction takes place at temperatures ranging from room temperatures to 150° C., and it should be carried out normally under the conditions of refluxing solvents. The reaction is usually completed in 30 minutes to 24 hours. The reaction solvent is concentrated and purified with normal treatment to give the thiophene derivatives expressed by the normal Formula (I).

Interconversion reactions of the substituent of the tiophene derivatives represented by $R_1$ in Formula (I) can be performed in the following manners. A trialkylsilyl group for $R_1$ in the thiophene derivative represented by Formula (I) is replaced by chlorine, bromine, iodine to give the thiophene derivative in which $R_1$ is chlorine, bromine, or iodine. In such a case, it is desirable to use halogen molecules in 1.5 to 2.5 equivalents to the thiophene derivative.

In the case of too excess of halogen molecules, β-site in a thiophene ring may be halogenated. Reaction solvents used are ether solvents such as dioxane and dimethoxyethylene, chlorine solvents such as chloroform, ethylenedichloride and carbontetrachloride, acids such as acetic acid and iodic acid, or a mixture of these. The reaction temperatures are most advantageously in the range of room temperature to 120° C., and the reaction time extends 30 minutes to 100 hours. The product is rinsed with water to remove the reaction solution and purified with a normal treatment process to give the thiophene derivative where $R_1$ is a halogen atom.

A hydrogen atom for $R_1$ in the thiophene derivatives expressed by Formula (I), is possible to replace by a halogen atom to give the derivatives in which $R_1$ is chlorine, bromine or iodine. This is a simillar procedure to that α-hydrogen atom in a thiophene ring is reacted with halogen molecules and replaced thereby, giving a halogen material. In this case, it is desirable to use the halogen molecules in 1.5 to 2.5 equivalents to the thiophene derivative. If halogen molecules are in too excess, β-site in a thiophene ring of the thiphene derivatives may be halogenated. The following solvents can be used for the reaction: ether solvents such as dioxane and dimethoxyethylene, chlorine solvents such as chloroform, ethylene dichloride and carbon tetrachloride, acids such as acetic acid and iodic acid, or a mixture of these. The reaction temperatures are most preferably range from room temperature to 120° C., and the reaction time extends 30 minutes to 100 hours. The product is rinsed with water to remove the reaction solution and purified with a normal treatment process to give the thiophene derivative where $R_1$ is the halogen atom.

Another method available consists of releasing α-hydrogen atom in the thiophene derivative with lithium diisopropylamine to give cation, and then replacing the same by a halogen atom. The amount of lithium diisopropylamine for the reaction is most preferably in equivalents of 2 to 2.5 to the thiophene derivative. The most desirable reaction solvents are diethylether, tetrahydrofuran and other ether solvents. It is preferable that reactions with lithium diisopropylamid take place at low temperatures. A reaction should be completed within one hour, preferably in 5 to 30 minutes. The addition of halogen molecules should be conducted at temperatures ranging from -80° C. to room temperatures; the temperatures should be as low as -80° C. to -40° C. at the start of the reaction, and should be increased slowly to room temperatures until the reaction ends. The best preferable reaction time is 1 to 24 hours. The product is rinsed with water to remove the reaction solution and purified with a normal treatment process to give the thiophene derivative in which $R_1$ is a halogen atom.

It is also possible to decompose with acid the trialkylsilyl group of the derivatives expressed by Formula (I) and to give the thiophene derivative with hydrogen as $R_1$. In this case, a trialkylsilyl compound is dissolved in benzene, toluene and other aromatic solvents, chloroform, ethylene di-chloride, carbon tetrachloride and other chloride solvents, and dioxane, dimethoxyethylene and other ether solvents. The resulting solution is stirred while hydrobromic acid and hydroiodic acid are added, and is then hydrolyzed. The most preferable reaction temperature is in the range of room temperatures to 120° C., and the amount of acids may be far in excess of their equivalent weight. The product is washed with water to remove the reaction solution, and then purified with a normal treatment process to give a thiophene derivative having a hydrogen atom as $R_1$.

Now, let us consider a case where for the derivatives expressed by Formula (I) in which $R_1$ is a halogen atom, including chlorine, bromine and iodine, such halogen atom is replaced by a trialkylsilyl group to produce the thiophene derivative with a trialkylsilyl group as $R_1$. The derivatives expressed by Formula (I) in which $R_1$ is a halogen atom is made into lithio product from alkyl-lithium, and with trialkylsilane halide added to the reaction solution, coupling is allowed to take place. Among the most preferred alkyllithiums for the reaction are n-butyllithium, s-butyl-lithium, and t-butyllithium. It is desirable to use alkyl-lithium in 2 to 2.5 equivalents to the thiophene derivatives. Ether solvents, including diethylether and tetrahydrofuran, are the most preferable reaction solvents. Lithionization with alkyl-lithium should be conducted below room temperatures, -80° C. to -40° C. in particular. It is desirable to complete a reaction within one hour. During coupling with trialkylsilyl halide added, temperatures should be in the range of -80° C. to room temperatures. They should be at low temperatures in the range of -80° C. to -40° C., and be increased gradually to room temperatures until the completion of the reaction. Most preferably, it should take one to 24 hours to complete a reaction. Examples of trialkylsilane halide for the reaction are trimethylsilylchloride, trimethylsilylbromide, t-butyldimethylsilylchloride, and t-butyldimethylsilylbromide. The trialkylsilane is used in equivalents of 2 to 3 to thiophene oligomer, the starting substance. The resultant product can be watered to remove the reaction solution and then purified with the normal treatment process.

The thiophene derivative by Formula (I) as produced by the aforestated procedure is extracted with a solution and purified by a normal treatment process, such as column chromatogram using slicagel or alumina, inverted-phase high-speed liquid chromatogram, and recrystalization. The thiophene derivative according to the present invention brings about light-induced ring closure reactions and shows changes in color. For this reason, it is desirable to conduct purification with light shut off.

As described in the following Formula,

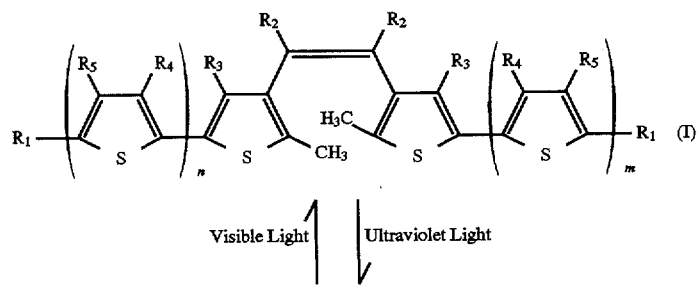

-continued

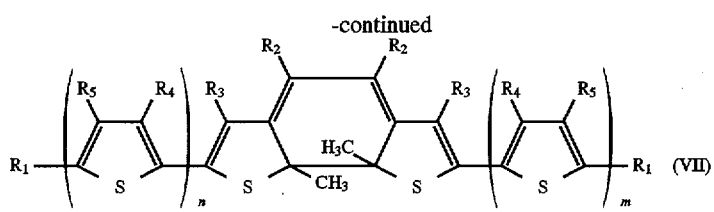

The thiophene derivative according to the present invention photoisomerizes to a ring closure product in Formula (VII) from a ring opening product in Formula (I) by irradiating ultraviolet light. The ring closure product absorbs light in longer wavelengths than the ring opening product. The ring opening product is colorless or yellow, while the ring closure product is highly colored or red, blue or green, etc. The colored ring closure product has high thermal stability, showing no change in color at a dark place for extended hours. When the ring closure product in Formula (VII) is irradiated with visible light, it reverses back to the ring opening product in Formula (I), and then their color disappears. The photochromism caused by this light-induced ring closure and ring opening can be considered to occur in a similar mechanism as with the diarylethene compound heretofore reported. The conventional reports on this subject include: Org. Chem., 53, 803–808 (1988), Bull. Chem. Soc. Jpn., 63, 1311–1315 (1990), and J. Phys. Chem., 96, 7671–7674 (1882). When the photochromism of the thiophene derivative according to the present invention is considered in terms of structural change of molecule, two side chains of the thiophene derivatives are twisted when in a ring-opening state. They are not conjugated and so the ring-opening state absorbs light in short wavelengths. While in a ring-closure state, they generally have a planar structure, the thiophene oligomer is considered to be conjugated and show long-wavelength absorption.

One of the features of the instant invention lies in the fact that as the thiophene oligomer chain contained in a thiophene derivative extends, the absorption bands of light ring-closure structure shift to longer wavelength bands, easily producing a photochromic compound with longer wavelength absorption bands. If this thiophene derivative according to the instant invention will be used as photochromic recording material, it can be made into a material for that application easily by the known process. For instance, the thiophene derivative according to the present invention is deposited onto an appropriate substrate by an evaporation method, or it is dissolved or dispersed in a solvent together with polyester resin, polystyrene resin, polyvinyl chloride, polyvinylbutyral resin, polymethylmethacryl acid ester resin, phenol resin and polycarbonate resin, with the resulting product coated onto an appropriate substrate. By these processes, photorecording layers are formed on the substrate for use as phtorecording material.

The thiophene derivative according to the present invention possesses a thiophene oligomer site which, like normal thiophene oligomers, is electrochemically oxidized to produce cation radicals. The oxidation potential tends to become low as the thiophene unit increases. By comparing the oxidation potentials of the ring-opening product in Formula (I) and the ring-closure product in Formula (VII), respectively, of the thiophene derivative material according to the present invention, it was observed that the oxidation potential of the ring-closure material is lower than that of the ring-opening product in Formula (I), by as much as 1V at the maximum. Like the observation as to absorption spectrum, this indicates that the two thiophene oligomer side chains are not conjugated in the ring-opening product, but that they are conjugated in the ring-closure product. Such large difference in oxidation potential between photoisomers testifies that the thiophene derivative according to the present invention acts as a switch to control oxidation potential with light.

If this thiophene derivative according to the instant invention is dissolved in an organic solvent containing a supporting electrolyte to build an electrochemical cell and a potential is established between the oxidation potentials of the ring-opening product and of the ring-closure product, no current flows for the ring-opening product (no oxidation occurs). When a ring-closure product is produced as a result of light irradiation, currents flow (oxidation takes place). This provides a switch system that can turn electric current on and off.

The thiophene derivative expressed by Formula (I) can change into this polymer. The substances represented by Formulas (VII)(IX) are polymers according to the present invention.

The polymers according to the present invention can be produced through electrolytic polymerization of the thiophene derivative expressed by Formula (I) in which $R_1$ is a hydrogen atom.

A derivative with a hydrogen atom as $R_1$ is dissolved in a solution containing a supporting electrolyte in a concentration of 0.01 to 1 mol $dm^{-3}$. The solvents used include acetonitrile, tetrahydrofuran, ethylene chloride, chloroform, ethylene dichloride, and plopyrene carbonate. For the supporting electrolyte, potassium toluene sulfonate acid, lithium perchlorate, lithium tetrafluoroborate, and other alkali metal salt, tetramethylammonium perchlorate, tetraethylammonium perchlorate, tetrabutylammonium perchlorate, tetramethylammonium tetrafluoroborate, tetraethylammonium tetrafluoroborate, tetrabutylammonium tetrafluoroborate, and other class 4 ammonium salt. The electrode used are of platinum, gold, palladium and other noble metals, or electrically conductive glass electrodes coated with gold, indium-tin oxide or tin oxide or electrically conductive plastic electrode. Voltages required for oxidation vary from compound to compound, but they generally range from 0.5 to 2.5V (the potential with respect to saturated calomel electrode). As stated above, compared with the ring-opening product expressed in Formula (I), the ring-closure product in Formula (VII) has a lower oxidation potential. Another way of saying this is that the ring-closure product expressed in Formula (VII) is more prone to be electrolytically polymerized at lower voltages.

Polymers obtained by the electrolytic polymerization process may be insoluble and infusible, in which case a film polymer is formed on the electrode. The polymer obtained here can be employed as modified electrode. The modified electrode obtained as a result of electrolytic polymerization of the ring-closure product of the thiophene derivative shows reversible oxidation-reduction reactions accompanying changes in color. The changes in color vary depending on the type of polymers, but oxidants tend to have absorption in longer wavelength bands than reductants.

The polymers expressed by Formulas (VII)(IX) according to the present invention can be obtained by the oxidative polymerization of a derivative expressed in Formulas (I) (VII) in which $R_1$ is a hydrogen atom.

For instance, these compounds are subject to chemical polymerization using an oxidizing agent.

The oxidizing agent is used in 0.8 to 5 equivalents for derivatives expressed in Formulas (I)(VII). Examples of the oxidizing agents include ferric chloride, sulfuric acid, and nitric acid. The solvents used are acetonitrile, tetrahydrofuran, ethylene chloride, chloroform, and ethylene dichloride. Reactions take place at temperatures from −40° C. to 30° C. It takes a few seconds to 12 hours to complete a reaction.

The derivatives expressed by Formulas (XII)(XIII) where R are a halogen atom by Formulas (I)(VII) can be chemically polymerized, using magnesium and nickel compounds, palladium compounds, cobalt compounds, iron compounds and other catalysts.

One equivalent of magnesium is allowed to react with the thiophene derivative expressed by Formulas (XII)(XIII) to give Grignard reagent. A catalyst in 0.001 to 0.1 equivalents are added to cause coupling. The catalysts are nickel dichloro (2,2'-bipyridine), nickel dichloride, nickel dichloro [1,3-bis (diphenylphosphino) propane] and other nickel compounds, palladium dichloro(2,2'-bi-pyridine), palladium tetra (triphenylphosphine) and other palladium compounds, cobalt chloride and other cobalt compounds, and iron compounds such as ferrite chloride. The solvents used are acetonitrile, tetrahydrofuran, methylene chloride, chloroform, and ethylene dichloride. A reaction takes place at temperatures ranging from room temperatures to approximately 120° C. It takes a few seconds to 12 hours to complete a reaction.

The polymers obtained by the chemical polymerization process according to the present invention are classified into two groups depending on the kind of their substituent groups $R_3$, $R_4$, and $R_5$, the insoluble and infusible polymers and the ones soluble in solvents. When one or more of the substituents $R_3$, $R_4$, and $R_5$ is a long-chain alkyl group with $C_7$ to $C_{20}$, including heptyl, octyl, nonyl, decyl, octadecyl and dodecyl, polymers soluble in solvents tend to be produced. If a polymer is insoluble and infusible, it is possible to purify it by filtering the reaction mixture. If a polymer is soluble in solvents, normal purification processes, such as extraction and gel filtration, are applicable. Polymers soluble in solvents have a molecular weight of some 1,000 to 50,000. The polymers soluble in solvents exhibit photochromism and electrochromism in a solvent.

[Operation]

As described above, the thiophene derivative according to the present invention provides a photochromic compound having a high thermal stability and a good repetitious durability against the development and disappearance of color, as well as an optical switch that can control oxidation-reduction response. It is possible, moreover, to easily polymerize the thiophene derivative according to the present invention by electrolytic polymerization or chemical polymerization. The resultant polymer also shows both photochromism and electrochromism, thus providing optical recording materials and photoelectroswitch materials.

Embodiments

With specific examples cited below, this invention will be described in further detail.

The chemical structure of the thiophene derivative according to the present invention is determined on the basis of mass analysis spectrum (MS), and nuclear magnetic resonance spectrum ($^1$H, $^{13}$C). Using a 500 W xenon lamp as a light source for photochemical measurement, the light emitted therefrom was passed through various glass filters to give ultraviolet light and visible light.

Example 1

Into a dry three-way flask, 3-bromo-2-methyl-5-trimethylsilylthiophene (4,99 g, 0.02 mol) and diethylether (100 ml) were placed and allowed to cool to −78° C. in an acetone-dry ice bath under an argon gas atmosphere. By adding sec-butyllithium (cyclohexane solution, 0.024 mol), the product was stirred for thirty minutes, and then was allowed to react at −78° C. for 2 hours by adding octafluorocyclopentene (1.4 ml,0.011 mol). The reaction product was heated to room temperatures, and the organic layer was extracted by adding water. The layer extracted was concentrated, and purified by alumina column chromatogram to give 1,2-bis(2-methyl-5-trimethylsilyl-3-thienyl) hexafluorocyclopentene (2.6 g, 0.005 mol).

m.p. 91.4° C.

MS(m/e) 513(M$^+$)

$^1$H-NMR (CDCl$_3$) 0.24(s, 18H), 1.89(s, 6H), 7.02 (s,2n)

$^{13}$C-NMR(CDCl$_3$) −0.3(s), 14.0(s), 111.3 (t, q), 116.3 (t, t), 126.6, 134.1, 136.6 (m), 138.8, 146.8

A hexane solution of this 1,2-bis(2-methyl-5-trimethylsilyl-3-thienyl)hexafluorocyclopentene (0.97×10$^{-5}$ mol dm$^{-3}$), which has Shoulder (ε=67400) absorption at 300 nm but is colorless, showed an absorption at 545 nm and assumed red, when irradiated by ultraviolet light. This spectral change was shown in FIG. 1. The absorption at 545 nm was considered attributable to the production of a ring-closure product due to a photo ring formation reaction. An acetonitrile solution (10 mmol dm$^{-3}$. including 0.1 mmol dm$^{-3}$ tetrafluoroammonium tetrafluoroborate as a supporting electrolyte) of 1,2-bis(2-methyl-5-trimethylsilyl-3-thienyl)hexafluorocyclopentene was examined for oxidation-reduction characteristics. It was found that the oxidation potential was 1.90V(Ag/AgClO$_4$) for the ring-opening product, while it was 0.89V(Ag/AgClO$_4$) for the ring-closure product.

Example 2

Into a dry three-way flask, 3-bromo-2-methyl-5-methylthiophene (10.3 g, 0,045 mol) and diethylether (200 ml) were placed and allowed to cool to −78° C. in an acetone-dry ice bath under an argon gas atmosphere. By adding n-butyllithium (hexane solution, 0.05 mol), the product was stirred for thirty minutes, then was allowed to react at −78° C. for 2 hours by adding octafluorocyclopentene (3.86 g, 0.02 mol). The reaction product was heated to room temperatures, and the organic layer was extracted by adding water. The layer extracted was concentrated, and purified by silica gel column chromatogram to give 1,2-bis(2-methyl-3-thienyl)-hexafluorocyclopentene (2.0 g, 0.0054 mol).

m.p. 73.6° C.

MS(m/e) 368(M$^+$)

$^1$H-NMR (CDCl$_3$) 1.83(s, 6H), 7.06(d, 2H), 7.16 (d,2H)

A hexane solution of this 1,2-bis(2-methyl-3-thienyl) hexafluorocyclopentene (1.0×10$^{-5}$ mol dm$^{-3}$), which has Shoulder (ε=68000) absorption at 295 nm but is colorless, showed an absorption at 505 nm and assumed red, when irradiated by ultraviolet light. The absorption at 505 nm was considered attributable to the production of a ring-closure product due to a photo ring formation reaction. An acetonitrile solution (10 mmol dm$^{-3}$. including 0.1 mmol dm$^{-3}$ tetrafluoroammonium tetrafluoroborate as a supporting electrolyte) of 1,2-bis (2-methyl-3-thienyl) hexafluorocyclopentene was examined for oxidation-reduction characteristics. It was found that the oxidation potential was 1.98V (Ag/AgClO$_4$) for the ring-opening product, While it was 0.71 V (Ag/AgClO$_4$) for the ring-closure product.

Example 3

Into a dry three-way flask, 3-bromo-2-methyl-5-(2-thienyl) thiophene (1.3 g, 0.005 mol) and diethylether (100 ml) were placed and allowed to cool to −78° C. in an aceton-dry ice bath under an argon gas atmosphere. By adding secbutyllithium (cyclohexane solution, 0.0058 mol), the product was stirred for thirty minutes, then was allowed to react at −78° C. for 2 hours by adding octafluorocyclopentene (0.48 g, 0.0025 mol). The reaction product was heated to room temperatures, and the organic layer was extracted by adding water. The layer extracted was concentrated, and purified by silica gel column chromatogram to give 1,2-bis[2-methyl-5-(2-thienyl)-3-thienyl] hexafluorocyclopentene (0.8 g, 0.0054 mol).

MS(m/e) 532 (M$^+$)

$^1$H-NMR (CDCl$_3$) 1.95(s, 6H). 7.00(dd, 2H), 7.11 (s,2H), 7.12 (dd, 2H), 7.24 (dd,2H)

A hexane solution of this 1,2-bis[2-methyl-5-(2-thienyl)-3-thienyl]hexafluorodyclopentene, which has an absorption at 322 nm but is colorless, showed an absorption at 605 nm and assumed blue, when irradiated by ultraviolet light. The absorption at 605 nm was considered attributable to the production of a ring-closure product due to a photo ring formation reaction. An acetonitrile solution (10 mmol dm$^{-3}$. including 0.1 mmol dm$^{-3}$ tetrafluoroammonium tetrafluoroborate as a supporting electrolyte) of 1,2-bis[2-methyl-5-(2-thienyl)-3-thienyl]hexafluorocyclopentene was examined for oxidation-reduction characteristics. It was found that the oxidation potential was 1.55V(Ag/AgClO$_4$) for the ring-opening product, while it was 0.63V(Ag/AgClO$_4$) for the ring-closure product.

Example 4

1,2-bis(2-methyl-5-trimethylsilyl-3-thienyl) hexafluorocyclopentene (2.16 g, 0.005 mol) was dissolved in chloroform (200 ml) and was allowed to react for 6 hours under refluxing conditions by adding concentrated hydrobromic acid (10 ml) to the solution. After the completion of the reaction, the chloroform layer was washed with an aqueous solution of sodium bicarbonate and the chloroform was removed under reduced pressures. The reaction product was purified by silicagel column chromatogram to give 1,2-bis(2-methyl-3-thienyl)hexafluorocyclopentene (1.8 g, 0.0049 mol).

Example 5

1,2-bis(2-methyl-5-trimethylsilyl-3-thienyl)hexafluorocyclopentene (5.25 g, 0.01 mol) was dissolved in chloroform (200 ml) and was allowed to react for 6 hours under refluxing conditions by adding bromine (3.2 g, 0.02 mol) to the solution. After the completion of the reaction, dioxane was added to water (2 l), and the organic layer was extracted with chloroform. The chloroform layer was washed with an aqueous solution of sodium bicarbonate to remove chloroform under reduced prepressures. The reaction product was purified by silicagel column chromatogram to give 1,2-bis (5-bromo-2-methyl-3-thienyl)hexafluorocyclopentene (2.1 g, 0.004 mol).

MS 524 (M$^+$), 526 (M$^{+2}$), 528 (M$^{+4}$)

$^1$H-NMR(CDCl$_3$) 1.87 (s, 6H), 6.91 (s, 2H)

Example 6

1,2-bis(2-methyl-3-thienyl)hexafluorocyclopentene (1.84, 0.005 mol) was dissolved in dioxane (200 ml) and was allowed to react for 6 hours under refluxing conditions by adding bromine (1.6 g, 0.01 mol) to the solution. After the completion of the reaction, dioxane was added to water (2 l), and the organic layer was extracted with chloroform. The chloroform layer was washed with an aqueous solution of sodium bicarbonate and then the chloroform was removed under reduced pressures. The reaction product was purified by silicagel column chromatogram to give 1,2-bis(5-bromo-2-methyl-3-thienyl)hexafluorocyclopentene (0.8 g, 0.0019 mol).

Example 7

Into a dry 300 ml three-way flask, 1,2-bis(5-bromo-2-methyl-3-thienyl)hexafluorocyclepentene (0.8 g, 0.0019 mol) and diethylether(100 ml) were placed and allowed to cool to −78° C. in an aceton-dry ice bath under an argon gas atmosphere. By adding n-butyllithium (hexane solution, 0.002 mol), the product was stirred for thirty minutes, then was allowed to react at −78° ° C. for 2 hours by adding trimethylsilylbromide (0.61 g, 0.004 mol). The reaction product was heated to room temperatures, and with water added thereto, the organic layer was extracted therefrom. The layer extracted was concentrated, and purified by alumina column chromatogram to give 1,2-bis(2-methyl-5-trimethlsilyl-3-thienyl) hexafluorocyclopentene (0.75 g, 0.0016 mol).

Example 8

1,2-bis(5-bromo-2-methyl-3-thienyl) hexafluorocyclopentene (2.1 g, 0.004 mol) obtained in EXAMPLE 5 was dissolved in dimethoxyethane (100 ml), paradium tetra(triphenylphosphine) (240 mg) was added to the mixture which was stirred for 5 minutes under argon atmosphere. With 5-trimethylsilyl-2-thienyl boric acid (2.0 g, 0.01 mol) and an aqueous solution of potassium carbonate (0.1 moldm$^{-3}$, 20 ml) were added, the reaction mixture was refluxed for two hours. It was then concentrated under reduced pressures, extracted with diethylether and rinsed with water. With the diethyether removed under reduced pressures, the product was purified by alumina column chromatogram to give 1,2-bis[2-methyl-5-(5-trimethylsilyl-2-thienyl)-3-thienyl]hexafluorocyclopentene (1.35 g, 0.002 mol).

MS 676 (M$^+$)

$^1$H-NMR(CDCl$_3$) 0.17 (18H, S), 1.51 (6H, S), 7.13 (2H, S) 7.23 (2H, d), 7.18 (2H, d)

A hexane solution of this 1,2-bis[2-methyl-5-(5-trimethylsilyl-2-thienyl)-3-thienyl)hexafluorocyclopentene, which has an absorption at 320 nm but is colorless, showed an absorption at 602 nm and assumed blue, when irradiated by ultraviolet light. The absorption at 602 nm was considered attributable to the production of a ring-closure product due to a photocyclization. An acetonitrile solution (10 mmol dm$^{-3}$. including 0.1 mmol dm$^{-3}$ tetrafluoroammoniumtetrafluoroborate as a supporting electrolyte) of 1,2-bis[2-methyl-5-(5-trimethylsilyl-2-thienyl)-3-thienyl]hexafluorocyclopentene was examined for oxidation-reduction characteristics. It was found that the oxidation potential was 1.57 V (Ag/AgClO$_4$) for the ring-opening product, while it was 0.63 V (Ag/AgClO$_4$) for the ring-closure product.

Example 9

Figure 2:
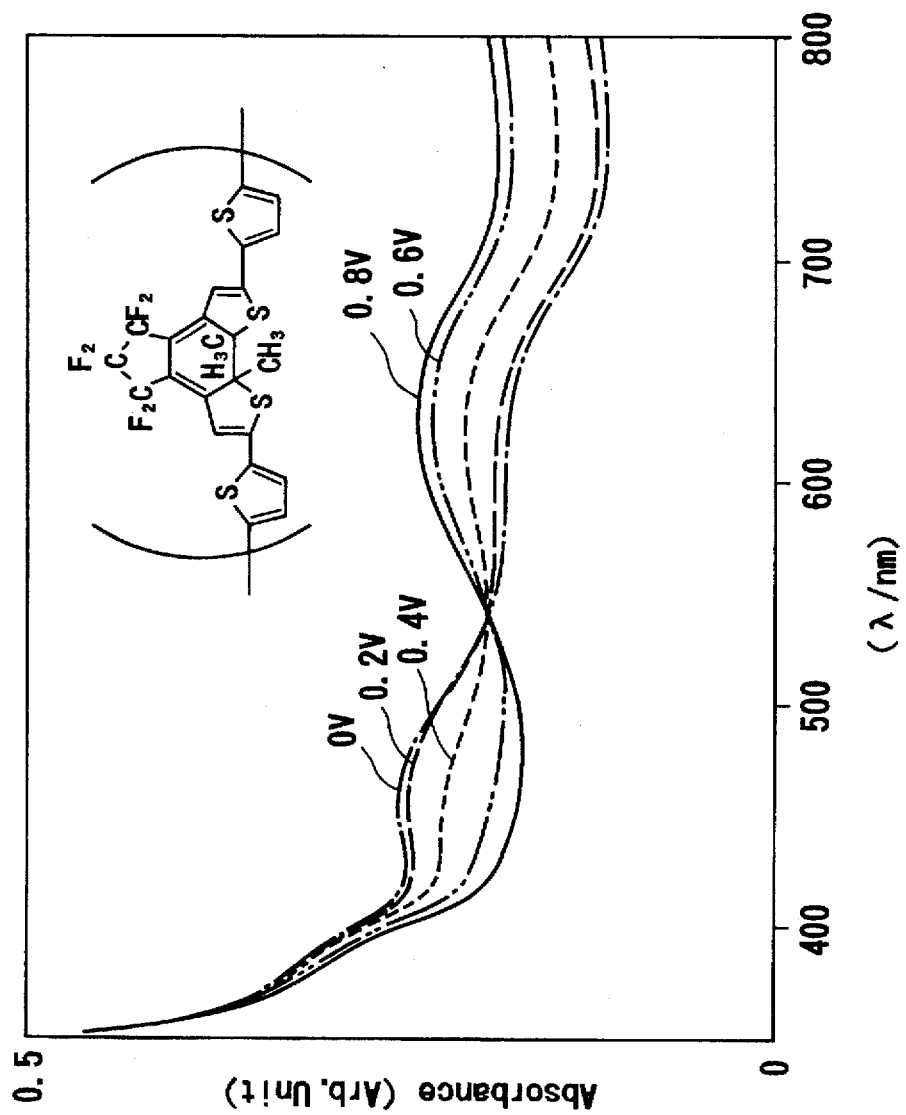
FIG. 2 shows an electrochromism of a ring-closure product due to re-oxidation as an example.

In an acetonitrile solution (10 mmol dm$^{-3}$, including 0.1 mol dm$^{-3}$ tetrafluoroammonium tetrafluoroborate as a supporting electrolyte) of 1,2-bis[2-methyl-5-(2-thienyl)-3-thienyl]hexafluorocyclopentene, electrolytic polymerization was carried out at an oxidation potential of 1.55 V (Ag/AgClO$_4$) using a glass electrode coated with indium-tin oxide (ITO). The result was the formation of a yellow polymer film on the ITO electrode. In the case of a ring-closure product induced by irradiation of ultraviolet light was electrolytically polymerized at 0.8 V, a dark blue polymer film was formed. This film polymerized from the ring-closure product showed electrochromism in which it assumed red as a result of electrochemical reduction, and turned blue by re-oxidation, as indicated in FIG. 2.

Example 10

1,2-Bis(5-bromo-2-methyl-3-thienyl)hexafluorocyclopentene (1.0 g 0.002 mol) was dissolved in dimethoxyethane (50 ml), and palladium tetra (triphenylphosphine) (120 mg) was added to the mixture which was stirred for 5 minutes under argon atmosphere. With 4-methyl-2-thienyl boric acid (852 mg, 0.006 mol) and an aqueous solution of potassium carbonate (0.1 mol dm$^{-3}$, 10 ml) were added, the reaction mixture was refluxed for two hours. It was then concentrated under reduced pressures, extracted with diethylether and rinsed with water. With the diethylether removed under reduced pressures, the product was purified by alumina column chromatogram to give 1,2-bis[2-methyl-5-(4-methyl-2-thienyl)-3-thienyl]hexafluorocyclopentene (447 mg, 0.0008 mol).

MS 558 (M$^+$)

$^1$H-NMR (CDCl$_3$) 1.94 (s, 6H), 2.25 (s, 6H), 6.98 (s, 2H), 7.11 (s, 2H), 7.13 (s, 2H)

A hexane solution of this 1,2-bis[2-methyl-5-(4-methyl-2-thienyl)-3-thienyl]hexafluorocyclopentene, which has an absorption at 315 nm and assumes light yellow, showed an absorption at 600 nm and assumed blue, when irradiated by ultraviolet light. The absorption at 600 nm was considered attributable to the production of a ring-closure product due to a photo ring formation reaction. An acetonitrile solution (10 mmol dm$^{-3}$. including 0.1 mmol dm$^{-3}$ tetrafluoroammoniumtetrafluoroborate as a supporting electrolyte) of 1,2-bis[2-methyl-5-(4-methyl-2-thienyl)-3-thienyl]hexafluorocyclopentene was examined for oxidation-reduction characteristics. It was found that the oxidation potential was 1.48 V (Ag/AgClO$_4$) for the ring-opening product, while it was 0.58V(Ag/AgClO$_4$) for the ring-closure product.

Example 11

1,2-bis(5-bromo-2-methyl-3-thienyl)hexafluorocyclopentene (1.0 g, 0.002 mol) was dissolved in dimethoxyethane (50 ml), and palladium tetra (triphenylphosphine) (120 mg) was added to the mixture which was stirred for 5 minutes under argon atmosphere. With 4-methyl-2-thienyl boric acid (2.28 g, 0.006, mol) and an aqueous solution of potassium carbonate (0.1 moldm$^{-3}$, 10 ml) were added, the reaction mixture was refluxed for two hours. It was then concentrated under reduced pressures, extracted with diethylether and rinsed with water. With the diethylether removed under reduced pressures, the product was purified by alumina column chromatogram to give 1,2-bis[2-methyl-5-(3-stearyl-2-thienyl)-3-thienyl]hexafluorocyclopentene (520 mg, 0.0005 mol).

$^1$H-NMR (CDCl$_3$) 0.94 (t, 6H), 1.34 (m, 60H), 1.50 (s, 6H), 1.67 (h, 6H), 2.68 (t, 6H), 6.98 (d, 2H), 7.12 (s, 2H), 7.20 (d, 2H)

A hexane solution of this 1,2-bis[2-methyl-5-(3-stearile-2-thienyl)-3-thienyl]hexafluorocyclopentene, which has an absorption at 315 nm and assumes light yellow, showed an absorption at 600 nm and assumed blue, when irradiated by ultraviolet light. The absorption at 600 nm was considered attributable to the production of a ring-closure product due to a photocycrization. An acetonitrile solution (5 mmol dm$^{-3}$. including 0.1 mol dm$^{-3}$ tetrafluoroammoniumtetrafluoroborate as a supporting electrolyte) of 1,2-bis[2-methyl-5-(4-methyl-2-thienyl)-3-thienyl]hexafluorocyclopentene was examined for oxidation reduction characteristics. It was found that the oxidation-potential was 1.50 V (Ag/AgClO$_4$) for the ring-opening product, while it was 0.58V (Ag/AgClO$_4$) for the ring-closure product.

Example 12

1,2-bis(5-bromo-2-methyl-3-thienyl)hexafluorocyclopentene (1.0 g, 0.002 mol) was dissolved in dimethoxyethane (50 ml), and palladium tetra (triphenylphosphine) (120 mg) was added to the mixture which was stirred for 5 minutes under argon atmosphere. With 5-(5-trimethylsilyl-2-thienyl)-2-thienyl boric acid (1.4 g, 0.006 mol) and an aqueous solution of potassium carbonate (0.1 mol dm$^{-3}$, 10 ml) were added, the reaction mixture was refluxed for two hours. It was then concentrated under reduced pressures, extracted with diethylether and rinsed with water. With the diethylether removed under reduced pressures, the product was purified by alumina column chromatogram to give 1,2-bis[2-methyl-5{5-trimethylsilyl-2-thienyl)-2-thienyl}-3-thienyl]hexafluorocyclopentene (550 mg, 0.0007 mol).

MS (m/e) 784(M$^+$)

$^1$H-NMR (CDCl$_3$) 0.34 (s, 18H), 1.52 (s, 6H), 7.11 (d, 2H), 7.12 (s, 2H), 7.17 (d, 2H), 7.20 (d, 2H),

A hexane solution of this 1,2-bis[2-methyl-5{5-trimethylsilyl-2-thienyl)-2-thienyl}-3-thienyl] hexafluorocyclopentene, which assumes yellow, showed an absorption at 660 nm and assumed blue, when irradiated by ultraviolet light. The absorption at 880 nm was considered attributable to the production of a ring-closure product due to a photocyclization. An acetonitrile solution (5 mmol dm$^{-3}$. including 0.1 mol dm$^{-3}$ tetrafluoroammonium tetrafluoroborate as a supporting electrolyte) of 1,2-bis[2-methyl-5{5-trimethylsilyl-2-thienyl)-2-thienyl}-3-thienyl]

hexafluorocyclopentene was examined for oxidation-reduction characteristics. It was found that the oxidation potential was 1.1 V (Ag/AgClO$_4$) for the ring-opening product, while it was 0.50 V (Ag/AgClO$_4$) for the ring-closure product.

Example 13

A methylene chloride solution of this 1,2-bis[2-methyl-5{5-trimethylsilyl-2-thienyl)-2-thienyl}-3- thienyl] hexafluorocyclopentene was deaerated with argon gas, and the compounds contained therein were converted into a ring-closure product by irradiation of ultraviolet light. The solution assumed blue, and when ferric chloride was added to the solution, dark blue high polymers came to be precipitated. The high polymer materials produced from the ring-closure product were insoluble and infusible, and their absorption spetrum was found to be the same as that of blue and black film high polymers.

Example 14

50 mg of magnesium was placed in a well-dried three-way flask, and was heated and allowed to dry under nitrogen flow. A tetrahydrofuran anhydride solution (50 ml) of 1,2-bis(5-bromo-2-methyl-3-thienyl)hexafluorocyclopentene (1.0 g, 0.002 mol) was added to prepare Grignard reagent. The reagent was cooled to room temperatures, then 57 mg of nickel dichloro(2,2-bipyridine) was added thereto. The product was refluxed with heating for 5 hours. The reaction mixture purified in hydrochloric acid-methanol and the impurities were removed by filtration to give 0.5 g of brown polymer. Chloroform soluble part of the precipitate was extracted and was measured for $^1$H-NMR (CDCl$_3$); an absorption of a strength ratio of 3:1 was observed at 1.7 ppm and 7.2 ppm. Gel permeation chromatograpy (GPC) showed that the mean molecular weight was in the order of 1500.

As described in detail, the instant invention provides the thiophene derivative and the polymer thereof which will respond to light and electricity and which are best suited for use as photorecording materials and light-electricity conversion elements.

I claim:

1. A thiophene derivative expressed by the following formula (I):

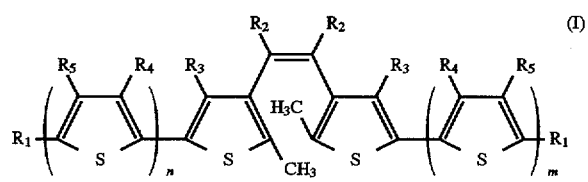

(I)

where n and m are independent integral numbers greater than 0; R$_1$ is hydrogen, halogen or trialkylsilyl; the R$_2$s, when taken together with the ethylenic linkage, form a ring and the R$_2$s taken together represent an optionally substituted alkylene group or a —COOCO— group, or each R$_2$ independently represents a cyano group; and R$_3$, R$_4$ and R$_5$ are independently selected from the group consisting of hydrogen and alkyl.

2. The method for producing a thiophene derivative expressed by the following formula (I):

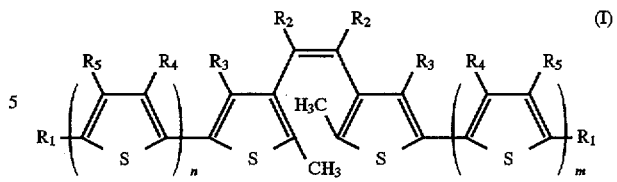

(I)

where n and m are independent integral numbers greater than 0; R$_1$ is hydrogen or trialkylsilyl; the R$_2$s, when taken together with the ethylenic linkage, form a ring and the R$_2$s taken together represent an optionally substituted alkylene group or a —COOCO— group, or each R$_2$ independently represents a cyano group; and R$_3$, R$_4$ and R$_5$ are independently selected from the group consisting of hydrogen and alkyl, comprising the step of:

allowing an alkene compound expressed by the following formula (II) to react with a thiophene compound expressed by formula (III) below,

(II)

where n and m are independent integral numbers greater than 0; R$_1$ is hydrogen atom, halogen or trialkylsilyl; the R$_2$s, when taken together with the ethylenic linkage, form a ring and the R$_2$s together represent an optionally substituted alkylene group or a —COOCO— group, or each R$_2$ independently represents a cyano group; and Z is a halogen atom,

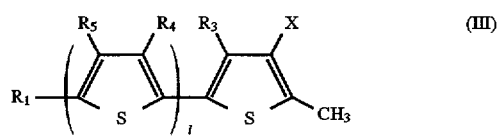

(III)

where 1 represents any integral number greater than 0; R$_1$ is hydrogen, halogen or trialkylsilyl; R$_3$, R$_4$ and R$_5$ are independently hydrogen or alkyl; and X is halogen.

3. The method for producing a thiophene derivative according to claim 2, wherein an alkene compound in formula (II) is perfluorocycloalkene which is expressed by the following formula (IV):

(IV)

where k is an integral number ranging from 2 to 4.

4. The method for producing a thiophene derivative according to claim 1, wherein R$_1$ is a hydrogen atom or a trialkylsilyl group, comprising the step of:

allowing an alkene compound expressed by the following formula (V) to react with a thiophene compound expressed by formula (VI) below,

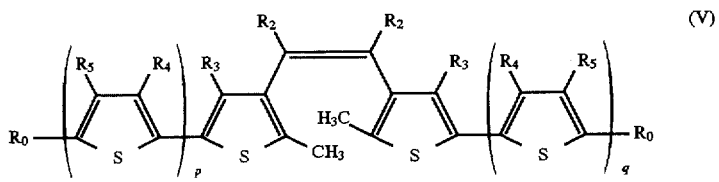

(V)

where p and q are independent integral numbers greater than 0; $R_0$ is halogen; the $R_2$s, when taken together with the ethylenic linkage, form a ring and together the $R_2$s represent an optionally substituted alkylene group or a —COOCO— group, or each $R_2$ represents cyano; and $R_3$, $R_4$ and $R_5$ are independently selected from the group consisting of hydrogen atom and alkyl.

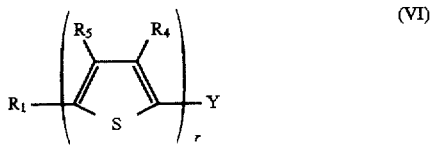

(VI)

where r represents any integral number greater than 0, $R_4$ and $R_5$ are as defined above; Y is selected from the group consisting of —$B(OH)_2$, a trialkyl tin moiety and a halogenated magnesium moiety; and $R_1$ is hydrogen or a trialkylsilyl.

5. The method for producing a thiophene derivative according to claim 1, wherein $R_1$ is a halogen atom, comprising the step of converting compounds of formula (I) wherein $R_1$ is hydrogen or trialkylsilyl to compounds of formula (I) wherein $R_1$ is halogen.

6. The method for producing a thiophene derivative according to claim 1, wherein $R_1$ is hydrogen, comprising the step of decomposing by acidification the compounds of formula (I) wherein $R_1$ is trialkylsilyl.

7. The method for producing a thiophene derivative according to claim 1, wherein $R_1$ is trialkylsilyl, comprising the step of converting compounds of formula (I) wherein $R_1$ is a halogen to compounds of formula (I) wherein $R_1$ is trialkylsilyl.

8. The thiophene derivative expressed by the following formula (VII):

9. The method for producing a thiophene derivative according to claim 8, wherein the thiophene derivative in formula (I)

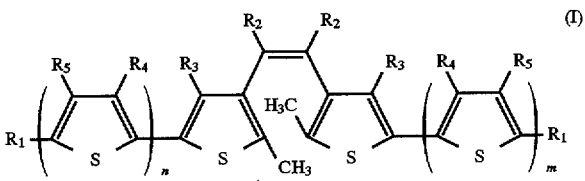

(I)

where n and m are independent integral numbers greater than 0; $R_2$ is hydrogen, halogen or trialkylsilyl; the $R_2$s, when taken together with the ethylenic linkage, form a ring and together the $R_2$s represent an optionally substituted alkylene group or a —COOCO— group, or each $R_2$ independently represents cyano; and $R_3$, $R_4$ and $R_5$ are independently selected from the group consisting of hydrogen and alkyl, is irradiated with ultraviolet rays for photoisomerization.

10. The method for producing a thiophene derivative according to claim 1, wherein the thiophene derivative expressed by the formula (VII)

(VII)

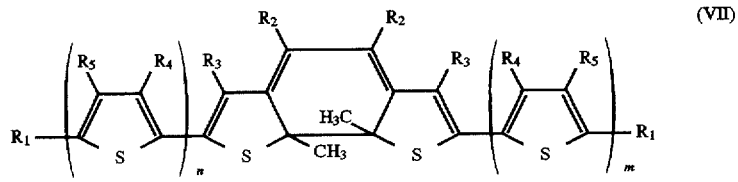

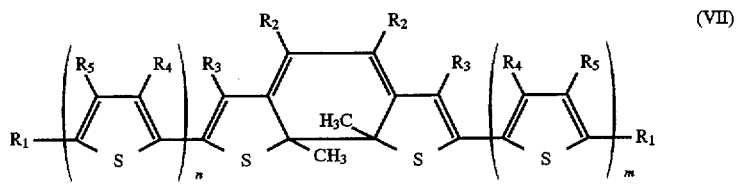

is irradiated with visible light for photoisomerization.

11. A polymer of a thiophene derivative of formula (VIII) or (IX):

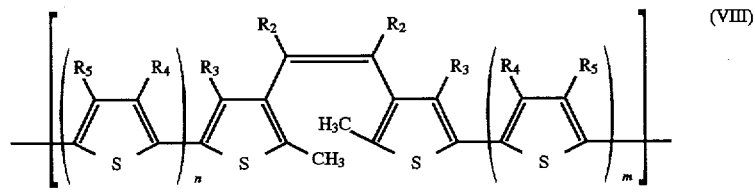

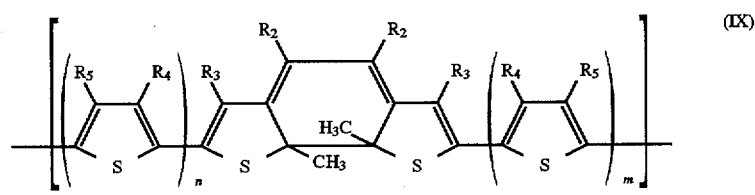

where n and m are independent integral numbers greater than 0; $R_1$ is hydrogen, halogen or trialkylsilyl; the $R_2$s, when taken together with the ethylenic linkage, form a ring and together the $R_2$s represent an optionally substituted alkylene group or a —COOCO— group, or each $R_2$ independently represents a cyano group; and $R_3$, $R_4$ and $R_5$ are independently selected from the group consisting of hydrogen and alkyl.

12. The method for producing a polymer of a thiophene derivative according to claim 11, comprising the step of polymerizing electrolytically or through oxidation of a thiophene derivative expressed by the following formula (X) or (XI):

13. The method for producing a thiophene derivative polymer according to claim 11, comprising the step of chemically polymerizing a thiophene derivative expressed in the following formula (XII) or (XIII):

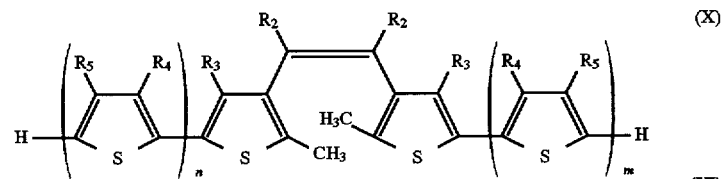

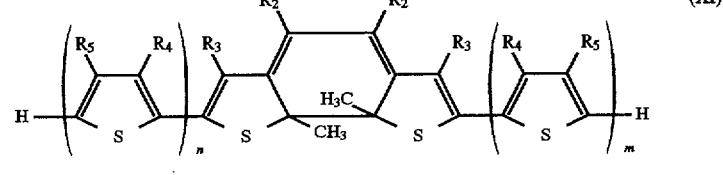

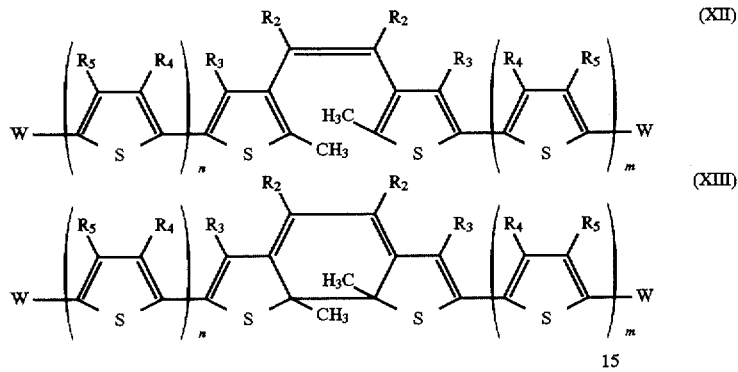
where W is halogen.
* * * * *